United States Patent [19]

Kruger

[11] 4,058,539

[45] Nov. 15, 1977

[54] 4,6,8(14)-TRIENE STEROIDS

[75] Inventor: Gunther Kruger, St. Laurent, Canada

[73] Assignee: Steele Chemicals Co. Ltd., Pointe Claire, Canada

[21] Appl. No.: 696,616

[22] Filed: June 16, 1976

Related U.S. Application Data

[63] Continuation-in-part of Ser. No. 497,691, Aug. 15, 1974, abandoned, which is a continuation-in-part of Ser. No. 215,669, Jan. 5, 1972, Pat. No. 3,849,402.

[30] Foreign Application Priority Data

Jan. 6, 1971  Canada ................................. 102448

[51] Int. Cl.$^2$ ........................... C07J 1/00; C07J 21/00

[52] U.S. Cl. ...................... 260/397.45; 260/239.55 R; 260/397.3; 260/397.5

[58] Field of Search .................. 260/397.45, 239.55 R, 260/397.5 R

[56] References Cited

U.S. PATENT DOCUMENTS 3,849,402  11/1974  Kruger ........................... 260/239.55

*Primary Examiner*—Elbert L. Roberts
*Attorney, Agent, or Firm*—McFadden, Fincham & Co.

[57] ABSTRACT

There are provided novel 4,6,8(14)-triene-steroids as well as processes for preparing such compounds. The above compounds are useful as intermediates in the preparation of other steroids, which in turn, may be converted into valuable pharmaceutical agents.

33 Claims, No Drawings

4,6,8(14)-TRIENE STEROIDS

This application is a continuation-in part of Ser. No. 497,691, filed Aug. 15, 1974, now abandoned which in turn is a continuation-in-part of Ser. No. 215,669, filed Jan. 5, 1972, issued as U.S. Pat. No. 3,849,402 on Nov. 14, 1974.

This invention relates to steroid compounds.

More particularly, one aspect of this invention relates to novel processes for preparing compounds of Formula (I). According to a still further aspect of the present invention, there are provided novel chemical compounds of the formula (Ia) useful as intermediates in the preparation of other compounds which may, in turn, be used as valuable starting materials for the production of pharmaceutically active compounds.

From the literature, it is reported in the J.O.C. (J. Elks) 468 (1954) and from J.C.S. (P. Bladon) 2176 (1955) and as well J.C.S. (P. Bladon and T. Sleigh) 6991 (1965), and in addition from J.O.C. (W. F. Johns) 31, 3780 (1966), that certain 10α- and 10β-methyl- as well as 10β-hydrogen steroids can be converted to the corresponding 4,6,8 (14) -trien-3-ones. The methods used to employ such triene compounds involve long and complicated chemical reaction routes and result in low yields of the end products. In addition, certain of those techniques employ starting materials which are not readily available.

Briefly summarized, the above prior art techniques may be grouped into three different types of processes: (a) converting 5,7-dien-3-ol acetates to the corresponding 5,8-peroxides which may then be further converted to the corresponding 8-hydroxy-4,6-dien-3-ones, which upon dehydration yield the corresponding above-mentioned triene compounds; (b) converting the alcohols, instead of the acetates of (a), into the above-mentioned trienones by treatment with para-benzoquinone and aluminum tert.-butoxide, there is obtained the above-mentioned triene compounds; and (c) converting 4,8 (14) -dien-3-ones into the corresponding above-mentioned trienes by treatment with a dehydrogenating agent. In the case of method (a), the process involved in complicated and the overall yield of triene is very low. In the case of method (b), starting from the alcohols, the yields are extremely low (in the order of about 5%); while in the case of method (c), the steroidal dienes used as starting materials are only difficulty obtainable.

In accordance with one aspect of the present invention, the novel products have formula (Ia) as follows:

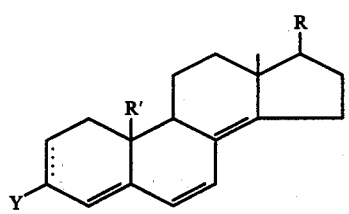
(Ia)

wherein Y is selected from the group consisting of keto, OH, O-acyl wherein acyl is as defined below, O-alkyl wherein alkyl is as defined below and H and wherein R is selected from the group consisting of O-Z;

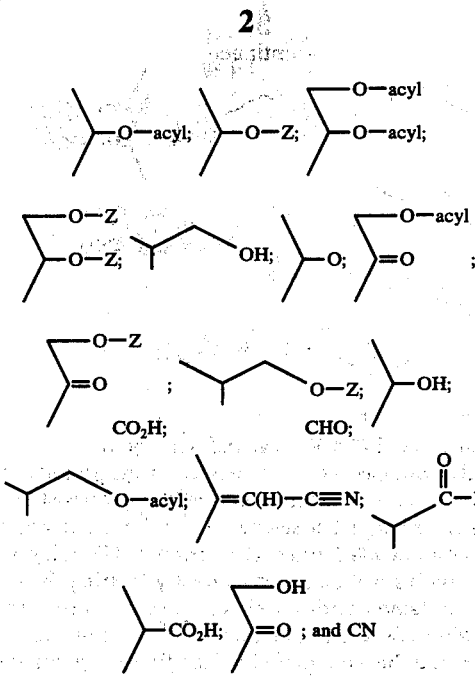

wherein Z represents tetrahydropyranyl, lower alkyl, preferably methyl, or a substituted methyl wherein the substituent is selected from the group consisting of phenyl, halogen, preferably chlorine and bromine, methoxy, $CH_2=CH$ and $HC\equiv C$; acyl represents a group selected from those consisting of acetate, trilower-alkyl acetates wherein the lower alkyl group is preferably methyl or ethyl, monohalo acetates and trihalo acetates, preferably wherein the halogen is Cl and Br, and R' is $CH_3$; $CH_2OH$; $CH_2-O-\!-\!-NH-C(CH_3)_3$; $CH_2OCOCH_3$; $CH_2OCHO$; CHO and H, and the dotted lines, as used in this specification, represent an optional double bond when Y is not keto.

In accordance with a further aspect of this invention, there are provided processes for preparing the above compounds, and in general those of formula (I);

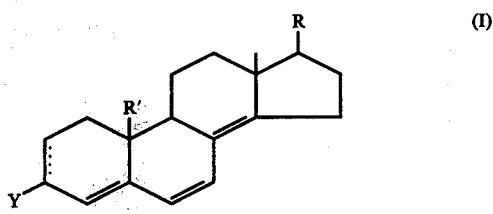
(I)

wherein R is selected from the group consisting of O-acyl or O-Z; OH; O;

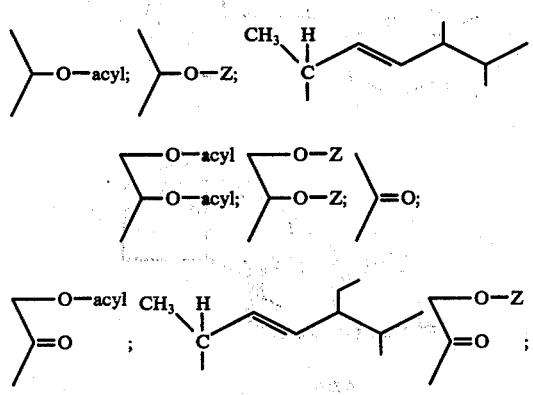

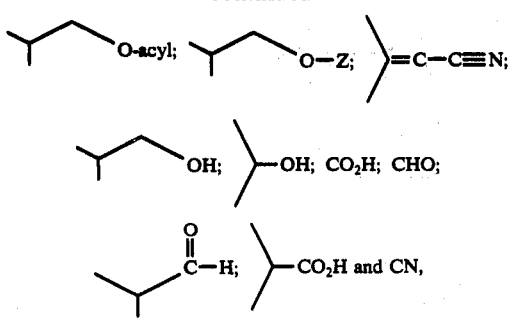
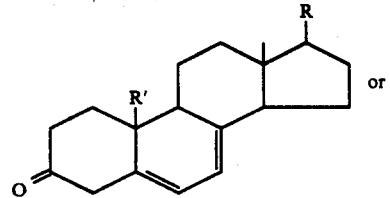

wherein Z, acyl and R' is as defined above.

Briefly summarized a process according to the present invention is selected from the group consisting of:

1. treating a member selected from the group consisting of compounds having the formula (II); (III); (IV) and (V) with a base, and subsequently treating the basic mixture obtained with a dehydrogenating agent and a weak acid to obtain a compound of the formula (I). The reaction may be exemplified by the following equation;

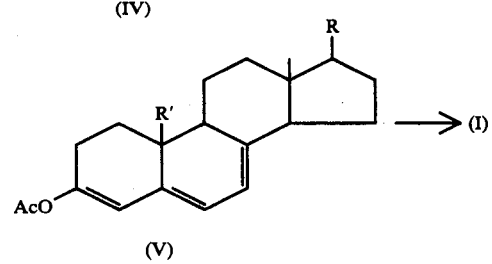

wherein
R and R' are as defined above;

2. reacting a compound of the formula (III); (IV); or (V) with a dehydrogenating agent to yield a compound of the formula (I) according to the following equation:

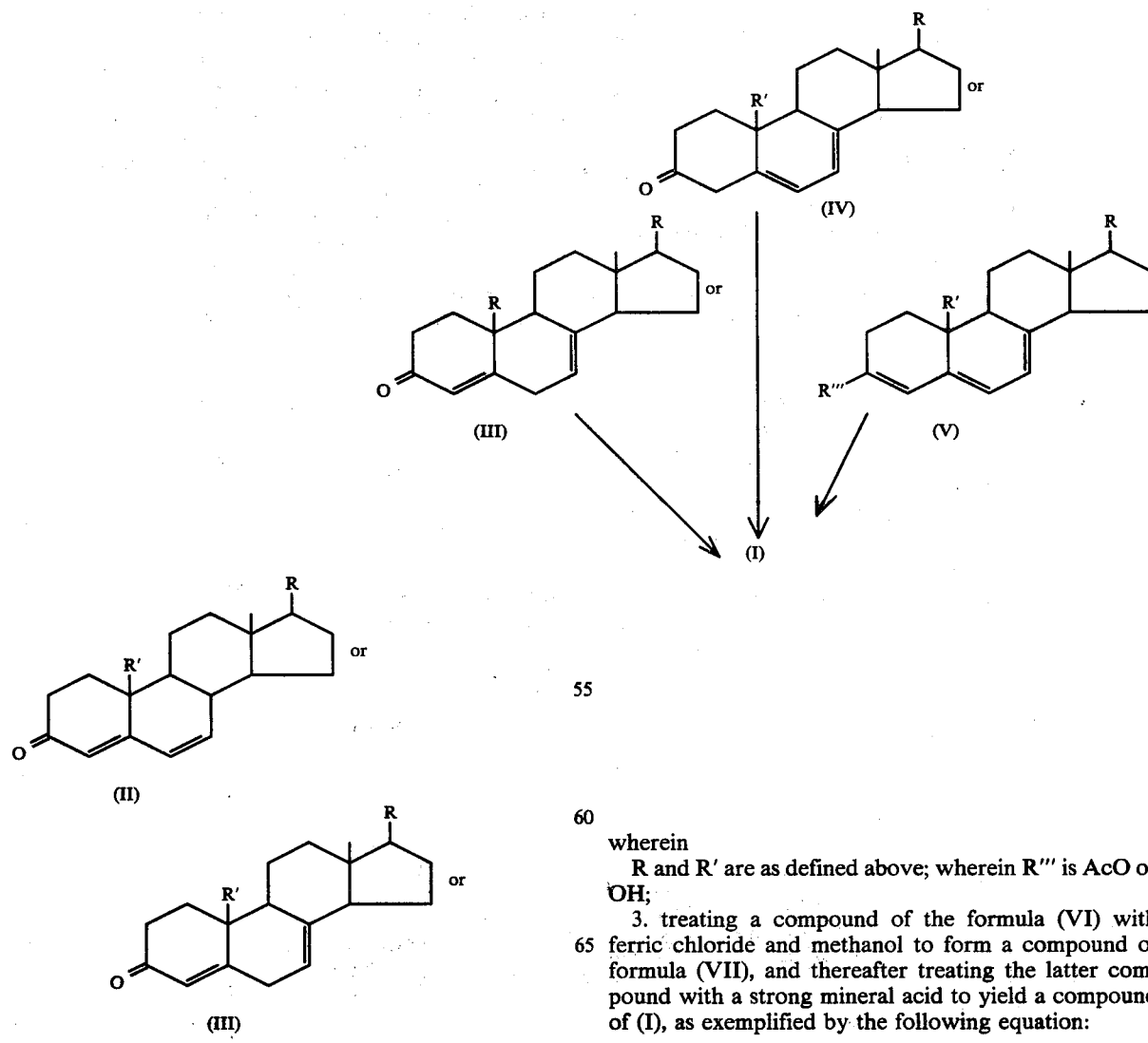

wherein
R and R' are as defined above; wherein R''' is AcO or OH;

3. treating a compound of the formula (VI) with ferric chloride and methanol to form a compound of formula (VII), and thereafter treating the latter compound with a strong mineral acid to yield a compound of (I), as exemplified by the following equation:

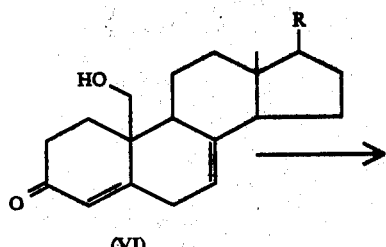

(VI)

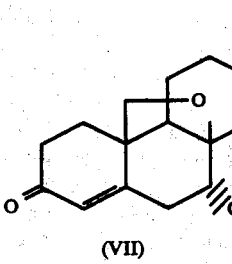

(VII)

wherein
R is defined above and Y is methyl;

4. treating a compound of the formula (VI) with a peracid to form a mixture of compounds having the formulae (VIII) and (VII) (wherein Y is H), and if desired, separating the compound of the formula (VII) from said reaction mixture, and if desired, acetylating the 7-hydroxy compound (VII) to a 7-acetoxy compound of formula (VII) wherein Y = COCH$_3$; thereafter treating the separated 7-hydroxy compound or the mixture of the latter and compound (VIII) or the 7-acetate (VII) with a strong mineral acid to form a compound of formula (I) according to the following equation:

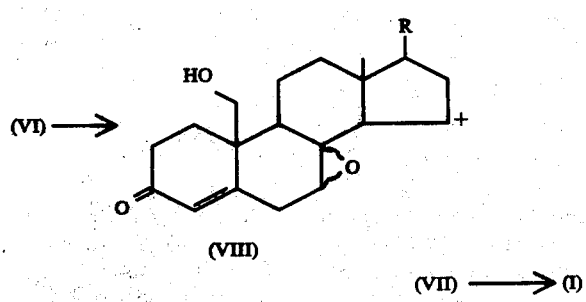

(VII) $\longrightarrow$ (I)

where
R is defined above;

5. treating a compound of the formula (VIII) + (VII) with a base to obtain a compound of the formula (IX) and the corresponding 8α-hydroxy compounds of the formula (X) and subjecting the products obtained to treatment with a dehydrating agent to yield a compound of formula (I), according to the following equation:

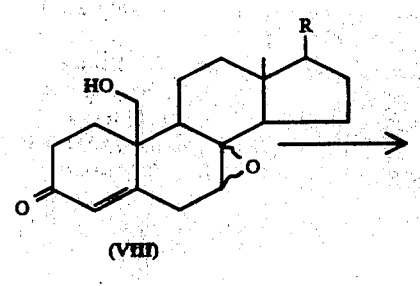

(VIII)

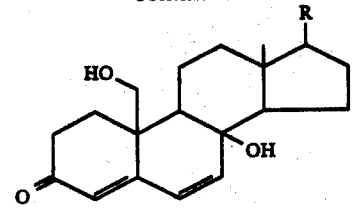

(IX)

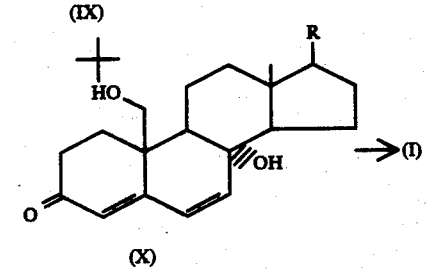

(X)

wherein
R is as defined above;

6. reacting a compound of the formula (XI) with a peracid to yield a compound of the formula (XII), thereafter treating the latter compound with a base to yield a compound of the formula (X) and then treating this compound with a dehydrating agent to yield a compound of the formula (I); all according to the following equation:

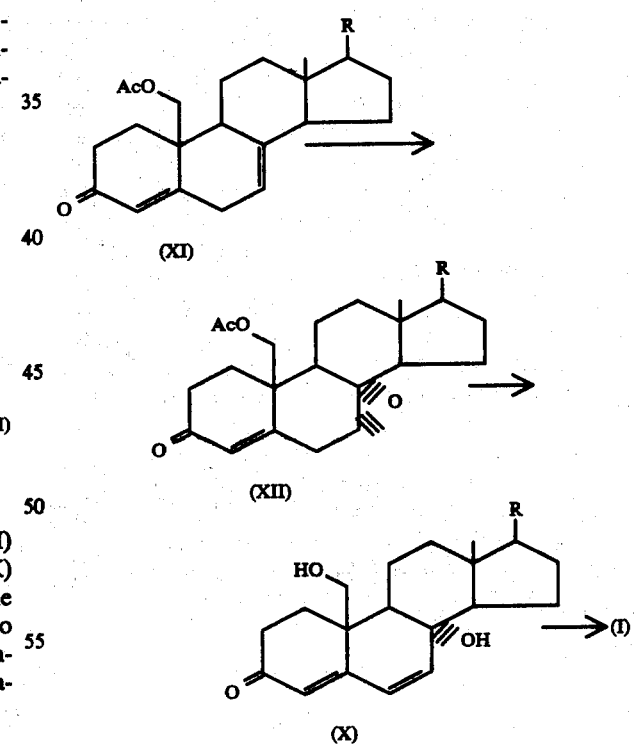

wherein
R is as defined above; and 7. treating a compound of the formula (XIII) with a peracid to yield a compound of the formula (XIV), reacting the latter compound with a base to yield a compound of the formula (XV) and thereafter dehydrating the latter to yield a corresponding compound of the formula (I), according to the following equation:

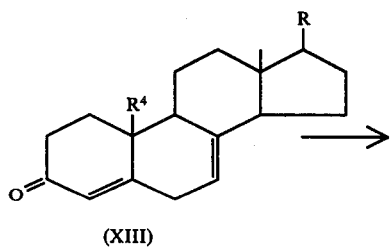

(XIII)

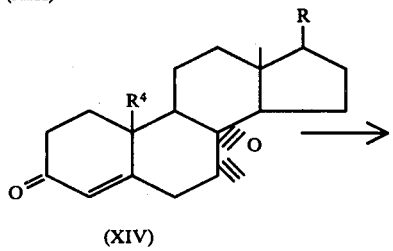

(XIV)

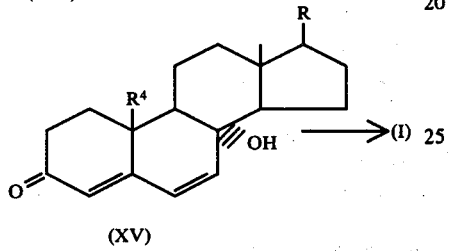

(XV)

wherein R⁴ is H; CH₃; or CH₂—O—CO—NH—C(CH₃)₃ and R is as defined above.

The 4,6,8 (14) -trien-3-ones of formula (Ia) and (I) may then be converted into the corresponding analogs of formula (Ia) and (I) in which Y is OH, Oacyl, O-alkyl or H, and in which there may be present the optional double bond in position 2. This treatment of a trienonone with a metal hydride can afford the corresponding 3-hydroxy analog of formula (I) or (Ia) which on acylation or alkylation by standard procedures can afford the corresponding 3-acyloxy or 3-alkyloxy analogs of formula (I) or (Ia). Dehydration of a 3-hydroxy-3-acyloxy or 3-alkyloxy analog of formula (I) or (Ia), e.g., under acidic conditions, can afford the corresponding 2-dehydro analog of formula (I) or (Ia) in which Y is H. Selective hydrogenation of the double bond in position 2 of the latter can afford the corresponding triene analog of formula (I) or (Ia), which has no functional groups in the 3- or 2-position. Treatment of a 4,6,8 (14) -trien-3-one with an enol acylate under acidic conditions can afford a 2-dehydro analog of formula (I) or (Ia) in which Y is O-acyl.

A preferred embodiment of the present invention relates to products having the formula

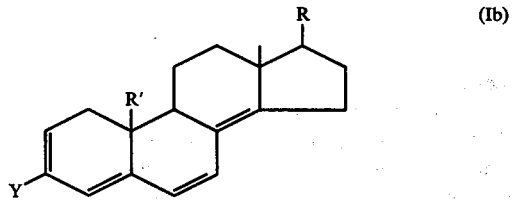

(Ib)

wherein R is selected from the group consisting of O—Z;

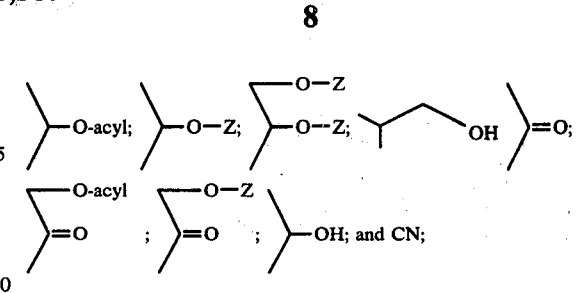

and Y represents a member selected from the group consisting of H or O-acyl; wherein Z is tetrahydropyranyl, lower alkyl, or substituted methyl wherein the substituent is selected from the group consisting of phenyl, halogen, methoxy, CH₂=CH and HC≡C; acyl represents a group selected from those consisting of acetate, trilower-alkyl acetates, monohalo acetates, trihalo acetates, and R' is selected from the group consisting of CH₂OH and CHO.

A still further preferred embodiment of this invention are compounds of the formula

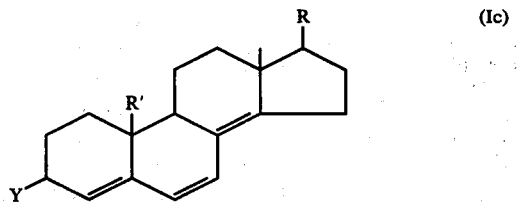

(Ic)

wherein R is selected from the group consisting of O-Z;

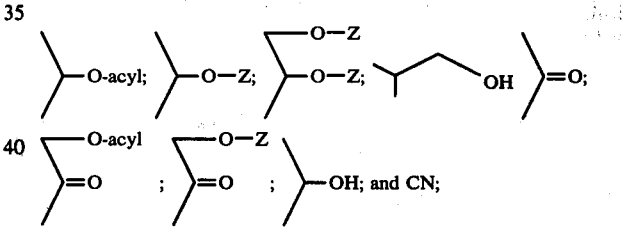

and Y represents a member selected from the group consisting of keto, OH, H, O-Z and O-acyl; wherein Z is tetrahydropyranyl, lower alkyl, or substituted methyl wherein the substituent is selected from the group consisting of phenyl, halogen, methoxy, CH₂=CH and HC≡C; acyl represents a group selected from those consiting of acetate, trilower-alkyl acetates, monohalo acetates, trihalo acetates, and R' is selected from the group consisting of CH₂OH and CHO.

With the above preferred embodiment of formula I(b), particularly preferred embodiments are where the group Z is tetrahydropyranyl; preferred embodiments for compounds of formula I(c) include those compounds where the group Z is methyl, or substituted methyl wherein the substituent is selected from the group consisting of phenyl, chlorine, bromine, methoxy, CH₂=CH and HC≡C.

In the above formulae, acyl is preferably an acetyl group or a trimethylacetyl group.

Other preferred embodiments of formulae I(a) through I(c) are the species wherein the compound is 19-hydroxy-20β-pivaloxypregna-4,6,8(14)-triene; 3β,19-dihydroxy-20β-pivaloxy-pregna-4,6,8(14)-triene; 19-hydroxy-20β-pivaloxypregna-2,4,6,8(14)-tetraene;

19-formyloxy-20β-pivaloxypregna-2,4,6,8(14)-tetraene; 3β,19-dihydroxy-17β-pivaloxyandrosta-4,6,8(14)-triene; 3β,17β,19-trihydroxyandrosta4,6,8(14)-triene; 3β,17β-19-triacetoxyandrosta 4,6,8(14)-triene; 19-hydroxy-17β-pivaloxyandrosta-4,6,8(14-trien-3-one; 19-hydroxy-17β-oxo-androsta-4,6,8(14)-trien-3-one; 17β,19-dihydroxyandrosta-4,6,8(14)-trien-3-one; 19,20β-dihydroxypregna-4,6,8(14)-trien-3-one; 19-hydroxy-20β-pivaloxypregna-4,6,8(14)-trien-3-one; 19-acetoxy-20β-pivaloxypregna-4,6,8(14)-trien-3-one; 19-formyloxy-20β-pivaloxypregna-4,6,8(14)-trien-3-one; 19,21-dihydroxypregna-4,6,8(14)-trien-3,20-dione; 3-oxo-20β-pivaloxypregna-4,6,8(14)-trien-19-al; and 3β,19,20β-trihydroxy-pregna-4,6,8(14)-tiene. A preferred proccess embodiment of the present invention is represented by the following:

A process for preparing a 4,6,8(14)-triene steroid compound of the formula

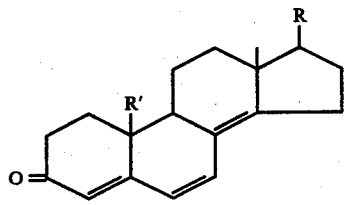 (I)

wherein R is selected from the group consisting of O-acyl; O-Z; OH; O;

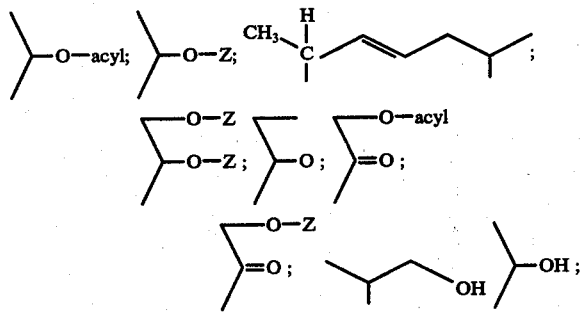

and CN; wherein Z is selected from the group consisting of tetrahydropyranyl, lower alkyl and substituted lower alkyl, and acyl is selected from acetate, formate, tri-lower-alkyl acetate, monohalo acetate, or trihalo acetate, and wherein R' is selected from the group consisting of CH₂OH and CHO, which process comprises:

a. treating, with a base, a compound chosen from

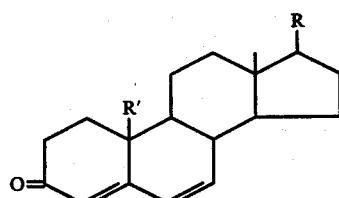 (II);

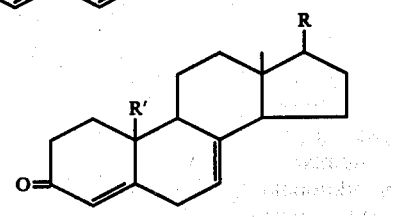 (III);

-continued

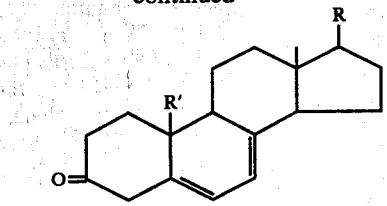 (IV);

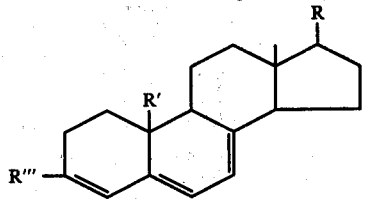 (V);

wherein R and R' are as defined above and R''' is AcO; and b. treating the resulting basic mixture with a dehydrogenating agent and a weak acid.

In greater detail, a preferred procedure for process (1) of the present invention is to employ an alkali metal alkoxide, or an alkali metal hydroxide; typical examples of which are sodium methoxide, sodium ethoxide, potassium tertiary butoxide, sodium hydroxide, potassium hydroxide, etc. Preferably the treatment with the base is carried out at approximately room temperature, although higher and lower temperatures may be employed if desired. The reaction is preferably carried out in the presence of an aprotic polar solvent, typical examples of which are dimethylsulfoxide, and other alkylsulfoxides, etc. It is most desirable to carry out the treatment of compound (II) with the base in the presence of an inert atmosphere, such as a nitrogen atmosphere, in order to exclude aerial oxidation; however, this is not essential if the base treatment is carried out for a short duration only.

The acid and dehydrogenating treatments of the resulting basic mixture can be carried out at or below room temperature preferably below 0° C. The above treatment with acid and dehydrogenating agent may also be carried out in the presence of a solvent, which may or may not be the same solvent used for the alkali treatment initially. Preferably, however, a water immiscible solvent is employed, such as ethyl acetate or ether, etc. As the acid employed, weak acids such as acetic acid, formic acid, propionic acid, as well as weak inorganic acids such as phosphoric acid, phosphonic acid, sulphorous acid, etc. may be employed. As the dehydrogenating agent, there may be employed various compounds such as dichlorodicyanoquinone, chloranil, benzoquinone, manganese dioxide, etc. The weak acid and the dehydrogenating agent may be suitably employed as a mixture of these ingredients in the solvent, or alternately, the basic mixture may first be treated with the acid and subsequently with the dehydrogenating agent.

The compounds of the formula (II) used as the starting materials for this reaction are known in the art, and reference may be had to "Steroids", volume 1, 1963, page 233 et seq, Fieser and Fieser, Steroids,, p. 555 (1959), Steroids, 1, 233 (1963), J.O.C. 29, 60 (1964), Experientia, volume 18, 1962, page 464.

Process (2) of the present invention involving the dehydrogenation of compounds of formula (III) to (V) into the corresponding compounds of formula (I) may be carried out at between room temperatures to elevated temperatures. The dehydrogenation is preferably carried out in an inert solvent, and any suitable solvent may be employed for this purpose. To this end, typical of the solvents which may be employed in the process of the present invention, are toluene, xylene, benzene, tertiary-butanol, etc. The dehydrogenating agent may be any suitable agent, typical agents being those mentioned above with respect to process (1). The compounds of formulae (III) and (V) are known in the art and are described in Fieser and Fieser, Steroids, page 111 (1959), J.O.C. 17, 134 (1952), and Tetrahedron Letters, No. 8, 387 (1964).

In carrying out process (3) according to the present invention, the first stage of converting a compound of the formula (III) wherein R' is CH$_2$OH, into a compound of the formula (VII) may be carried out at room temperature, preferably in the presence of an inert solvent. Preferably the reaction is carried out under anhydrous conditions employing anhydrous solvents and reagents for the same reason.

The treatment of the compound (VII) to yield a compound of formula (I), is preferably carried out with a strong mineral acid, such as hydrobromic acid, perchloric acid, hydrochloric acid, etc. The reaction may be carried out in the presence of an inert solvent, a typical solvent being, for example, ether or ethyl acetate. The reaction may expediently be carried out at room temperature, or elevated temperatures may be employed, if desired.

Carrying out process (4) of the present invention as described above, a compound of formula (VI) is treated with a peracid preferably in the presence of a solvent. Typical solvents include, for example, carbon tetrachloride, benzene, hexane, methanol, etc. Reaction temperatures may range from below to above room temperature. The peracid employed in this reaction may be any suitable peracid, typical examples being perbenzoic acid, meta-chloroperbenzoic acid, peracetic acid, trifluoroacetic acid, etc. The starting materials employed in this reaction are a species of the formula (III) and may be prepared as described above with respect to such compounds.

The product resulting from the above-described reaction may consist of a mixture of a compound of the formula (VII), wherein the radical Y is H, with the compound of the formula (VIII) from which there may be separated, if desired, the compound of formula (VII), which may be converted to a compound of the formula (I) by treatment with a mineral acid as described above with respect to the conversion of a compound of the formula (VII) according to process (3) of the present invention. If the mixture is not separated, the total mixture of compounds of the formula (VII) and (VIII) may be treated with a strong mineral acid as described with respect to process (3) of the present invention, to form the corresponding compound of formula (I).

If desired, the compound of formula (VII) separated from the reaction mixture of compounds of the formula (VII) and (VIII) may be acetylated by conventional means using conventional acetylating agents, such as for example, acetic anhydride, pyridine, etc.; whereupon there is obtained a compound of formula (VII) in which Y radical y is the acetyl group. This latter compound may then be converted into a compound of the formula (I) by treatment with mineral acid as described in process (3) hereinabove.

In carrying out process (5) according to the present invention, the compound of the formula (VIII) separated from the above-described mixture of compounds of formulae (VII) and (VIII) may be treated with a base, such as for example, sodium hydroxide, potassium hydroxide, sodium carbonate, etc. preferably in a solvent such as an alcoholic solvent — e.g. ethanol, methanol, etc. to form a mixture of a compound of the formula (IX) and its α-isomer of formula (X). The mixture may be separated into the respective isomers if desired, and those isomers subsequently subjected to a dehydrating agent, or alternately, both isomers forming the mixture may be treated. The dehydration may be carried out according to conventional techniques and procedures well known to those skilled in the art.

The process of the present invention described under (6) above may be carried out by treating a compound of the formula (XI) with a peracid using, for example, the reagents and conditions described with respect to process (4) above, whereupon a compound of the formula (XII) is obtained. Compound (XII) may then be treated with a base as described likewise in process (5) for the conversion of the compound of the formula (VIII) to compounds of formulae (IX) and (X), whereupon there is obtained the α-isomer of the formula (X). Thereafter, this α-isomer may be treated as described above with respect to process (5) with a dehydrating agent according to conventional procedures and techniques to obtain a compound of the formula (I) or (Ia).

The compounds of the formula (XI) are a species of the compounds of the formula (III) and may be prepared as described above.

As outlined above with respect to process (7), a compound of the formula (XIII) is initially subjected to treatment using a peracid as, for example, the peracids described with respect to process (4) to yield a compound of the formula (XIV). The latter compound may then be treated with a base such as those described in connection with process (5) (wherein a compound of the formula (VIII) is converted to a mixture of compounds of formulae (IX) and (X)) thereby to obtan a compound of the formula (XV), which may be treated with a dehydrating agent according to conventional procedures and techniques to obtain a compound of the formula (I). One of the starting materials used in this process (7) may be obtained by treating a compound of the formula (III) with tertiary-butyl isocyanate at an elevated temperature (e.g. at about 100° C.) whereupon the compound of the formula (III), wherein R' is CH$_2$—O—CO—NH—C(CH$_3$)$_3$, is obtained; the others may be obtained as described with respect to compound III.

The various processes of the present invention possess several unexpected and advantageous features. Thus, with regard to process (1), it has been observed that $\Delta^{4,6}$-3-keto steroids undergo 1,2-dehydrogenation only independent of the nature of the dehydrogenating agent used as stated by Fieser and Fieser, Reagents for Organic Synthesis, p. 216, 1967 and as evident from Djerassi, Steroid Reactions, p. 231 and p. 233. In conrast, the method of process (1), in which the $\Delta^{4,6}$-3-keto steroid is sbjected to alkali treatment before addition of the dehydrogenating agent to the reaction mixture, affords $\Delta^{4,6,8(14)}$-3-keto steroids independent of whether, for example, dichlorodicyanoquinone or chloranil is used as the dehydrogenating agent.

With respect to process (2), according to Tetrahedron Letters, number 8, 387 (1964), one would ordinarily expect an additional double bond to be introduced into the 1 position when starting from a 4,7-diene and employing dichlorodicyanoquinone as the reagent in conjunction with an inert solvent; however, contrary to this expectation, and according to the process of the present invention, there is surprisingly obtained a 4,6,8 (14)-triene-3-one.

With respect to process (3), by treating a compound of the formula (VI) according to the process, the cyclization of the γ, δ -unsaturated alcohols to an α-methoxy tetrahydrofuran analog of the formula (VII) is completely unexpected and no reference is known in the literature for this type of conversion. Furthermore it is also surprising that the latter compound can be cleanly converted into the desired end products despite of considerable reorganization of the molecular structure of the intermediate. This latter transformaion is still further surprising due to the fact that it can be carried out at room temperature under relatively mild conditions, whereas one would have ordinarily expected tetrahydrofuran ethers to require more severe conditions for the cleavage of the ether bond.

With respect to process (4), no references appear to exist for the conversion of 19-hydroxy 4, 7-dienes-3-ones into 7-hydroxy-8, 19-oxido 4-ene-3-ones and as discussed with respect to process (3) it is surprising that these α-substituted tetrahydrofuran compounds may be cleaved to the compounds of formula (I) under relatively mild conditions.

Likewise, with respect to process (5), it is unexpected that one can obtain an 8 β-hydroxy-compound in which there is present a β-hydroxy methyl group in position 10, and a β-methyl group in position 13, since conformational analysis would predict a severe steric interaction of the last two mentioned substituents, with the 8β-hydroxy group. Further, with regard to processes (5), (6) and (7), the literature does not indicate any prior teachings that 19-hydroxy and other 19- and 10-substituted 7,8-oxido-4-ene-3-ones yield 8,19-dihydroxy-4,6-dien -3-ones under mild basic conditions.

It is still further surprising that the oxides of processes (5), (6) and (7) do not undergo rearrangement under the reaction conditions and that the reaction is selective with respect to the 7 double bond while the double bond in position 4 remains unaffected. As reported in, for example, "Steroids", Fieser and Fieser, page 243 (1959), 7,8-oxides undergo rearrangement to 7-hydroxy-8,14-enes under epoxidation conditions. The compounds of this invention are even more highly unstable than those of the reference because they possess a 4-en-3-one group in close proximity to the 7,8-oxide ring, while in the compounds of the reference such destabilising groups are absent.

The novel products of the present invention of formula (Ia), as well as those produced by the process of the present invention and being of the formula (I), are very valuable as intermediaes for the preparation of compounds of the formula

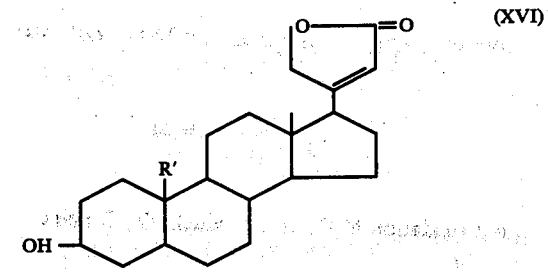

(XVI)

wherein R' is as defined above.

The use of such compounds and their glycosides for the treatment of cardiac insufficiency is well known, as for example disclosed in Angewandte Chemie vol. 9, No. 5, pp 321–332. Conventionally, such 14β-hydroxycardenolides have been isolated from natural sources. Recently a number of 14β-hydroxycardenolides have also been obtained by synthesis using as key intermediates 14β-hydroxypregnan-20-ones or pregn-14-en-20-ones. These synthetic methods are, however, not economical and afford only cardenolides having a methyl group in position 10. In contrast, there have subsequently been developed novel methods for the preparation of valuable 3, 14β-oxygenated precursors, to 14β-oxygenated cardenolides as described in copending Ser. No. 215,669, filed Jan. 5, 1972, now U.S. Pat. No. 3,849,402.

As is obvious to those skilled in the art, these precursors can readily be converted into the corresponding 14β-hydroxycardenolides by taking recourse to one of several of the well known previously developed methods for such conversions. The methods of the copending patent application are distinquished by their simplicity and economy and also allow the preparation of variously functionalized cardenolides, such as, for example, 19-oxygenated cardenolides, 19-noncardenolides and unsaturated cardenolides. This functionalization makes it possible to bring about a medicinally desirable change in the kind and degree of cardiac activity. For example, studies on differently substituted cardenolides isolated from natural sources have shown that 19-oxygenated cardenolides are substantially more active than their 19-methylanalogs, as described in Fieser and Fieser, Steroids, Chapter 20.

In the synthetic routes of the methods disclosed in the copending application the 4,6,8(14)-trien-3-ones of this invention function as important intermediates to the above 3,14β-oxygenated precursors.

In greater detail, as disclosed in said copending application the compounds of the present invention may, for example, be converted to the corresponding analogous 3-hydroxy-8(14)-enes by reduction of the 3-keto group in conjunction with the selective hydrogenation of the 4- and 6-double bonds. Subsequent introduction of the 14β-hydroxy group is then accomplished by several methods. The above conversions are depicted by the following scheme:

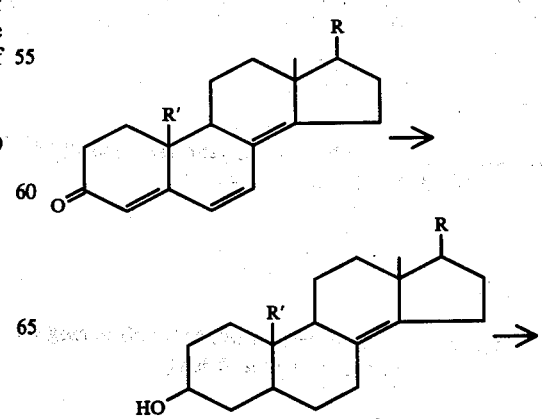

-continued

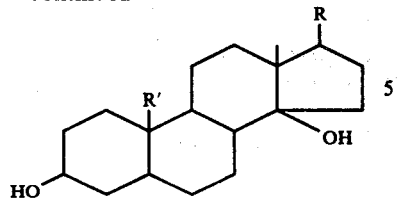

The conversion of the group R in position 17 of the latter 3,14β-oxygenated precursors into the 17β-butenolide ring of the compounds of formula (XVI) may then be carried out according to methods known to those skilled in he art, as for example summarized in Angewandte Chemie (supra). Thus, for instance, 14β-hydroxy-17β-acetyl- as well as 14β-hydroxy-21-acetoxy-17β-acetyl steroids have been converted into 14β-hydroxy compounds having a butenolide ring in the 17β-position via initial transformaion into the corresponding 20-ethoxyacetylen 20-ol and successive acid treatment and oxidation with selenium dioxide in boiling benzene, as described by F. Sondheimer, Chemistry in Britain, Vol. 1, No. 10, pp 454–464 (1965). While in the above method the butenolide side chain is introduced subsequent to the introduction of the 14β-hydroxy group, in other methods, as for example, described in Angewandte Chemie (supra), the 17β-butenolide side chain is introduced into compounds not possessing a 14β-hydroxy group which is introduced in the final step.

With regard to the other groups in the 17β-position, as specified above for general formula (I), where the group R is

CH₂Oacyl—CO
        | it may be converted into the butenolide ring by the method described above for the transformation of a 21-acetoxy -17β-acetyl steroid (R is CH₂OAc—CO).
           |

Where the group R is

CH₂Oalkyl—CO
         | it may be first converted to a group R where it is

CH₂OH—CO
       | by conventional methods. Subsequent acetylation affords then the above 21-acetate (R is CH₂OAc—CO)
           | which then can be converted to the butenolide ring as described above. In the case where R is

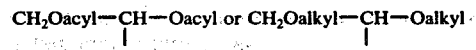
CH₂Oacyl—CH—Oacyl or CH₂Oalkyl—CH—Oalkyl
         |                    | conversion of these groups by conventional methods into group R where it is

CH₂OH—CHOH
       | followed by selective aetylation in position 21 and subsequent oxidation of the 20-hydroxy group by the method described, for example, in F. Sondheimer, Chemistry in Britain, cited above, affords then a group R which is

CH₂OAc—CO,
        | which may be converted to a butenolide ring according to the methods described above.

In the case where R is

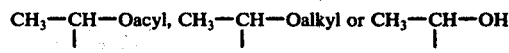
CH₃—CH—Oacyl, CH₃—CH—Oalkyl or CH₃—CH—OH
     |              |              | conventional procedures, such as used for the generation of hydroxy groups from acylates and ethers respectively and subsequent oxidation, afford a 17β-acetyl group

(where R is CH₃—CO),
              | which may be converted to the butenolide ring by methods described above.

In the case where R is

CH₃—CH—CHO
     | the 17β-butenolide ring may be formed by conventional cyanohydrin formation followed by dehydration and conversion of the α, β-unsaturated nitrile obtained into the corresponding α, β-unsaturated 23-carboxylic acid ethyl ester, again by conventional methods, and subsequent treatment with selenium dioxide in boiling benzene as described by F. Sondheimer, Chemistry in Britain, cited above. In the case where R is

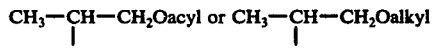
CH₃—CH—CH₂Oacyl or CH₃—CH—CH₂Oalkyl
     |                  | conversion to the corresponding 22-alcohol, where R is

CH₃—CH—CH₂OH
     | and oxidation to the above aldehyde, R being

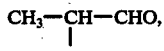

by conventional methods, may then afford the 17β-butenolide ring by the method described above. In the case where R is

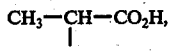

reduction of the carboxylic acid group to the above 22-aldehyde by conventional methods may then subsequently afford the 17β-butenolide ring by the method described above.

In the case where R is

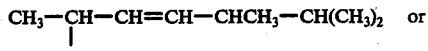 or

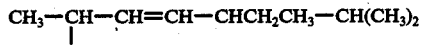

ozonolysis of the 20(22)- double bonds, as described, for example, by A.F. Daglish J. Chem. Soc., pp 2627–2633 (1954) affords then the above 22-aldehyde R being

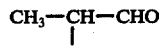

which may then be converted to the butenolide ring by the method described above.

In the case where R is CN, conventional transformation to the corresponding methyl ester, R being

followed by conversion of the latter to a butenolide ring may be accomplished as described by F. Sondheimer, Chemistry in Britain, cited above. In the case where R is O= formation of the corresponding cyanohydrin followed by conventional dehydration and hydrogenaion, affords R being CN which can be converted to the 17β-butenolide ring as described above. In the case where R is OH, -Oacyl or -Oalkyl conversion of these groups into compounds where R is O= by conventional methods followed by application of the methods described above also yields the 17β-butenolide ring.

In a like manner, according to known techniques, the substituent R' in formulae (Ia) and (I) may be modified in the 10 position to convert the group R' intoanalogs having a different R' value, as defined hereinbefore, (see e.g. C. Djerasi, Steroid Reactions, Chapters 6 and 8).

Having thus generally described the invention, reference will nowbe made to the accompanying Examples illustrating representative preferred embodiments.

EXAMPLE 1

A solution of 15 g. of 19-hydroxy-17β-pivaloxyandrosta- 4,6-dien-3-one in 150 ml. of dimethyl sulfoxide was treated with 30 g. of soidum methoxide for 20 seconds under an atmosphere of nitrogen whereupon a solution was added, which consisted of 10.5 g. of dichlorodicyanoquinone, 1500 ml. of ether and 150 ml. of glacial acetic acid, and had been cooled below −60° C. The resulting mixture was stirred until it warmed to −10° C., whereupon a solution of 450 ml. of half saturated sodium bisulfite and 900 ml. of water was added in succession. The ethereal phase was then extracted several times with 2% aqueous potassium hydroxide until the extracts were alkaline. Evaporaion, addition of water and hexane, followed by filtration and recrystallization of the precipitate from ether-hexane gve the compound 19-hydroxy-17β-pivaloxyandrosta-4,6,8(14)-trien-3-one, mp 182°–183° C., λ max 341 mμ

EXAMPLE 2a

A solution of 200 mg. of 19-hydroxy-17β-pivaloxyandrosta-4,6-dien 3-one in 2 ml. of dimethyl sulfoxide was treated with 400 mg. of sodium methoxide under nitrogen for 15 seconds. The mixture was then poured into 20 ml. of half-frozen 10% aqueous acetic acid, stirred for a few minutes under nitrogen and filtered to yield a precipitate, which had λ max 321 mμ and consisted essentially of 3,19-dihydroxy-17β-pivaloxyandrosta-3,5,7-triene. The latter product was then treated with an equal amount of chloranil in 20 volumes of toluene at room temperature for 10 minutes. Extraction with aqueous potassium hydroxide and evaporation afforded 19-hydroxy-17β-pivaloxyandrosta-4,6,8(14)-trien 3-one as indicated by tlc and uv-spectroscopy.

EXAMPLE 2b

19-Hydroxy-17β-pivaloxyandrosta-4,6,8(14)-trien-3-one was also obtained, when the intermediate 3,19-dihydroxy-3,5,7-triene described in Example 2a, was subjected to the oxidation conditions of the Example, except that dichlorodicyanoquinone instead of chloranil was used.

EXAMPLE 3

A mixture of 100 mg. of 19-hydroxy-17β-pivaloxyandrosta-4,7-dien-3-one, 2 ml. of t-butanol and 100 mg. of chloranil was heated at 100° C. for 2 minutes, whereupon aqueous sodium bisulfite and aqueous sodium sulfite was added.

The mixture was then extracted with ether and the ethereal phase was extracted with 10% aqueous potassium hydroxide until the extracts were alkaline. The ethereal phase was then extracted with aqueous sodium bisulfite, subsequently dried with sodium sulfate, treated with charcoal, filtered through diatomaceous earth and evaporated to yield 19-hydroxy-17β-pivaloxyandrosta-4,6,8(14)-trien-3-one as indicated by tlc and uv-spectroscopy.

19-Hydroxy-17β-pivaloxyandrosta-5,7-dien-3-one and 3-acetoxy-19-hydroxy-17β-pivaloxyandrosta-3,5,7-triene when treated in the above manner, also yielded 19-hydroxy-17β-pivaloxyandrosta-4,6,8(14)-trien-3-one.

EXAMPLE 4

When the procedure of Example 1 was repeated except that 3-acetoxy-19-hydroxy-17β-pivaloxyandrosta-3,5,7-triene, 3,19-diacetoxy-17β-pivaloxyandrosta-3,5,7-triene, 19-hydroxy-17β-pivaloxyandrosta-4,7-dien-3-one or 19-hydroxy-17η-pivaloxyandrosta-5,7-dien-3-one was used as the starting material 19-hydroxy-17β-pivaloxyandrosta-4,6,8(14)-trien-3-one could also be obtained.

EXAMPLE 5

To a solution of 10 g. of 19-hydroxy-17β-pivaloxyandrosta-4,7-dien-3-one in 400 ml. of ethyl acetate and 100 ml. of methanol, was added 30 g. of anhydrous ferric chloride. The mixture was stirred for two and a half minutes whereupon a mixture of 34 ml. of concentrated ammonia and 150 g. of ice was added, followed by 300 ml. of water and 800 ml. of ethyl acetate. The mixture was agitated and filtered through diatomaceous earth, the organic phase was extracted several times with water, dried with sodium sulfate and evaporated at reduced pressure. The resulting viscous residue was treated with petroleum ether and the precipitate formed was filtered off. The filtrate was concentrated, petroleum ether was added and the mixture was left to stand at 0° C. Recrystallization of the precipitate obtained from petroleum ether afforded 7-methoxy-17β-pivaloxy-8,19-oxidoandrost-4-en-3-one, mp. 158° C., λ max 247 mμ. The structure of the compound was verified by nmr-spectroscopy and by elemental analysis.

EXAMPLE 6

A mixture of 10 mg. of 7-methoxy-17β-pivaloxy-8,19-oxidoandrost-4-en-3-one, 1 ml. of ether and 0.01 ml. of 48% aqueous hydrobromic acid was stirred for five and a half hours at room temperature. The organic phase of the mixture was extracted several times with water until the washings were neutral, and was then evaporated. Treatment of the residue with petroleum ether and subsequent filtration gave 19-hydroxy-17β-pivaloxyandrosta-4,6,8(14)-trien-3-one, as indicated by uv-spectroscopy and tlc.

EXAMPLE 7

To a mixture, consisting of 5 g. of 19-hydroxy-17β-pivaloxyandrosta-4,7-dien-3-one and 100 ml. of 95% aqueous methanol, was added 42.8 ml. of a solution prepared by addition of 37.8 ml. of 0.5 molar perbenzoic acid in methylene chloride to 8.9 ml. of 95% aqueous methanol. After standing at room temperaure for 48 hours, the solvents of the mixture were evaporated at reduced pressure at 40°-45° C. whereupon 500 ml. of ether was added. The organic phase was extracted three times with 2% aqueous potassium hydroxide until the extracts were alkaline, dried with sodium sulfate and evaporated. Treatment of the residue obtained with petroleum ether, followed by filtration gave a solid, mp. 196°-204° C., which consisted of a mixture of 7-hydroxy-8,19-oxido-17β-pivaloxyandrost-4-en-3-one, 19-hydroxy-7α,8α-oxido-17β-pivallxyandrost-4-en-3-one and 19-hydroxy-7β,8β-oxido-17β-pivaloxyandrost-4-en-3-one.

A solution of 500 mg. of the above product in 50 ml. of ether was treated with 1 ml. of 48% aqueous hydrobromic acid at 37° C. for three hours. The ethereal phas was washed with water and aqueous sodium bicarbonate, dried with sodium sulfate and concentrated. Petroleum ether was added and the resulting precipitate was filtered off. Recrystallization from ether-petroleum ether yielded 19-hydroxy-17β-pivaloxyandrosta-4,6,8(14)-trien-3-one as indicated by uv-spectroscopy and tlc. When 7-hydroxy-8,19-oxido-17β-pivaloxyandrost-4-en-3-one, which is a component of the mixture, was treated in the manner outlined above 19-hydroxy-17β-pivaloxyandrosta-4,6,8(14)-trien-3-one was also obtained and it is assumed that the isomeric 7α,8α- and 7β,8β-oxides similarly afford 19-hydroxy-17β-pivaloxyandrosta-4,6,8-(14)-trien-3-one.

EXAMPLE 8

A mixture of 500 mg. of the intermediate product of Example 7, consisting of 7-hydroxy-8,19-oxido-17β-pivaloxyandrost-4-en-3-one, 19-hydroxy-7α,8α-oxido-17β-pivaloxyandrost-4-en-3-one and 19-hydroxy-7β,8β-oxido-17β-pivaloxyandrost-4-en-3-one, 2 ml. of pyridine and 1 ml. of acetic anhydride was left to stand for 16 hours at room temperature, whereupon 80 ml. of water was added and the mixture was extracted with ethyl acetate. The organic phase was washed with water, dried and evaporated. The residue obtained was treated with cold ether-petroleum ether and the resulting precipitate was filtered. Recrystallization from ether-petroleum ether yielded 7-acetoxy-8,19-oxido-17β-pivaloxyandrost-4-en-3-one, mp. 163°-164° C. The structure of the latter compound was further verified by nmr-spectroscopy.

The above 7-acetate was treated with hydrobromic acid in ether under the conditions described in Example 6 afforded 19-hydroxy-17β-pivaloxyandrosta-4,6,8(14)-trien-3-one.

EXAMPLE 9

A solution of 2 g. of 19-hydroxy-17β-pivaloxyandrosta-4,7-dien-3-one in 2000 ml. of carbon tetrachloride was left to stand with 1.5 g. of meta-chloroperbenzoic acid for two and a half days, whereupon an additional 0.5 g. of meta-chloroperbenzoic acid was added. After five days the solution was repeatedly extracted with 2% aqueous potassium hydroxide until the extracts were alkaline. The solution was then extracted with water and evaporated. The residue obtained was treated with 9 ml. of 0.2 N methanolic potassium hydroxide for 30 minutes. Then 9 ml. of 0.2 N acetic acid in ethyl acetate was added and the mixture was concentrated at reduced pressure. Recrystallization of the residue combined with thick layer chromatography yielded 7-hydroxy-8,19-oxido-17β-pivaloxyandrost-4-en-3-one, mp. 211°-212° C. λ max 246 mμ, 8α,19-dihydroxy-17β-pivaloxyandrost-4,6-dien-3-one, mp 202°-203° C., λ max 280 mμ, as well as 8β,19-dihydroxy-17β-pivaloxyandrost-4,6-dien-3-one, mp. 218°-220° C., λ max 282 mμ. The structure of these compounds was confirmed by ir and nmr spectroscopy.

The first of the above three compounds may then be converted into 19-hydroxy-17β-pivaloxyandrosta-4,6,8(14)-trien-3-one by, for example, the procedure of Example 7.

The latter 8α- and 8β-hydroxy-4,6-dien-3-ones may be dehydrated to 19-hydroxy-17β-pivaloxyandrosta-4,6,8(14)-trien-3-one according to conventional techniques well known to those skilled in the art.

EXAMPLE 10

A mixture of 1 g. of 19-hydroxy-17β-pivaloxyandrosta-4,7-dien-3-one, 2 ml. of pyridine and 1 ml. of acetic anhydride was left to stand for twenty hours at room temperature under nitrogen whereupon 30 ml. of water was added. The precipitate, which gradually formed, was filtered and dried.

A mixture of 500 mg. of 19-acetoxy-17β-pivaloxyandrosta-4,7-dien-3-one, obtained as above, 550 mg. of meta-chloroperbenzoic acid and 25 ml. of methanol, containing 5% water, was left to stand for three days at approximately 35° C., whereupon 250 ml. of ether was added. The mixture was extracted with 2% aqueous potassium hydroxide until the extracts were alkaline. The organic phase was dried with sodium sulfate and evaporated. The residue obtained was then purified by thick layer chromatography to yield 19-acetoxy-7α,8α-oxido-17β-pivaloxyandrost-4-en-3-one.

A mixture of 90 mg. of the latter and 3.6 ml. of 0.2 N methanolic potassium hydroxide was left to stand for 40 minutes at room temperature whereafter 3.6 ml. of 0.2 N acetic acid in ethyl acetate was added. The mixture was then evaporated, treated with 1.8 ml. of water and 1.8 ml. of petroleum ether, and concentrated. The white precipitate obtained was filtered and then recrystallized from ether-methylene chloride to yield 8α,19-dihydroxy-17β-pivaloxyandrosta-4,6-dien-3-one, mp. 201°–203° C., which can then be dehydrated to 19-hydroxy-17β-pivaloxyandrosta-4,6,8(14)-trien-3-one according to conventional techniques.

EXAMPLE 11

A mixture of 1.5 g. of 19-hydroxy-17β-pivaloxyandrosta-4,7-dien-3-one and 22.5 ml. of t-butylisocyanate was heated at 95°–100° C. under nitrogen for two days, whereupon 45 ml. of hexane was added and the mixture was concentrated. Subsequent filtration yielded 19-hydroxy-17β-pivaloxyandrosta-4,7-dien-3-one N-t-butylcarbamate, mp 163°–167° C.

A solution of 1 g. of the latter product in 50 ml. of 95% aqueous methanol was treated with 800 mg. of meta-chloroperbenzoic acid for two days at 35° C. Thereafter an additional 400 mg. of meta-chloropenbenzoic acid was added; after standing for a further four hours, 500 ml. of ether was added and the organic phase was washed with aqueous potassium hydroxide, until the washings were alkaline. The organic phase was dried, evaporated, and the residue was treated with ether. Filtration of the precipitate formed yielded 19-hydroxy-17β-pivaloxy-7α,8α-oxidoandrost-4-en-3-one N-t-butylcarbamate, mp. 170°–174° C.

The latter product was then treated with methanolic potassium hydroxide and acetic acid in ethyl acetate as described in Example 10 for the analogous 19-acetate to yield, on working up, 8α,19-dihydroxy-17β-pivaloxyandrosta-4,6-dien-3-one 19-N-t-butylcarbamate as glassy material, λ max 279 mμ. The structure of the compound was confirmed by ir- and nmr-spectroscopy and by elemental analysis. The latter product may then be converted into 19-hydroxy-17β-pivaloxyandrosta-4,6,8(14)-trien-3-one N-t-butylcarbamate or into the corresponding 17- or 19-hydroxy analogs using conventional hydrolysis and dehydration methods respectively.

EXAMPLE 12

By following the procedure described in Example 1, but using as the starting material, 19-hydroxyandrosta-4,6-diene-3,17-dione, there was obtained 19-hydroxyandrosta-4,6,8(14)-trien-3,17-dione, mp. 264°–265° C., λ max 339 mμ.

EXAMPLE 13

By following the procedure described in Example 1, but using as the starting material 19-hydroxy-20β-pivaloxypregna-4,6-dien-3-one, there was obtained 19-hydroxy-20β-pivaloxypregna-4,6,8(14)-trien-3-one, mp. 221°–222.5° C., λ max 345 mμ.

EXAMPLE 14

By following the procedure described in Example 1 but using as the starting material 17β-pivaloxyestra-4,6-dien-3-one the compound 17β-pivaloxyestra-4,6,8(14)-trien-3-one, λ max 342 mμ, was obtained.

When the above starting material was substituted by 3-acetoxy-17β-pivaloxyestra-3,5,7-trien 17β-pivaloxyestra-4,6,8(14)-trien-3-one could also be obtained.

The latter starting material can be obtained by conventional enol acetylation with, for example, acetic anhydride, acetyl chloride and pyridine of 17β-pivaloxyestra-4,6-dien-3-one, which in turn can be prepared from 19-hydroxy-17β-pivaloxyandrosta-4,6-dien-3-one (see G. Kruger, J.O.C., in press) by oxidation to the corresponding 19-carboxylic acid, followed by decarboxylation according to procedures elaborated previously on analogous 19-hydroxyandrosta-4,6-dien-3-ones (see Helv. Chim. Acta, 50, 269 (1967)).

EXAMPLE 15

To 0.75 ml. of pyridine, which was cooled externally by an ice-bath, was added 750 mg. of chromium trioxide. The mixture was stirred for 5 minutes under nitrogen, whereupon a suspension of 500 mg. of 19-hydroxy-17β-pivaloxypregna-4,6,8(14)-trien-3-one in 5.0 ml. of pyridine was added. The mixture was stirred for 10 minutes and was then taken out of the ice-bath and stirred for a further 60 minutes whereupon 100 ml. of water and 100 ml. of hexane was added. A brown interphase appearing between the organic and aqueous phase was removed by filtration through celite. An excess of dilute hydrochloric acid was added and the organic phase was repeatedly extracted with water, dried with sodium sulfate and evaporated. The residue obtained was digested with pentane to yield the compound 3-oxo-20β-pivaloxypregna-4,6,8(14)-trien-19-al, mp. 106°–107° C.

The starting material of the above reaction was prepared from pregnonolone acetate by the method used for the preparation of the analogous 19-hydroxy-17β-pivaloxyandrosta-4,6-dien-3-one from androstenolone acetate as described in G. Kruger, J.O.C., in press.

EXAMPLE 16

A mixture of 20 mg. of 3-oxo-20β-pivaloxypregna-4,6,8(14)-trien-19-al in 0.2 ml. of 2 N methanolic KOH was shaken under nitrogen for 30 minutes whereupon an excess of dilute aqueous hydrochloric acid was added. Filtration followed by recrystallization of the precipitate obtained from methanol afforded 20β-pivaloxy-19-norpregna-4,6,8(14)-trien-3-one, mp. 182°–183° C., λ max 344 mμ.

EXAMPLE 17

A mixture of 20 mg. of 3β,17β,19-trihydroxyandrosta-4,6,8(14)-triene, 20 mg. of dichlorodicyanoquinone and 2.0 ml. of ether was shaken under nitrogen for 20 minutes. Subsequent filtration afforded the compound 17β,19-dihydroxyandrosta-4,6,8-(14)-trien-3-one, λ max 344 mμ.

The preparation of the starting material of the above reaction is described in copending patent application Ser. No. 215,669, filed Jan. 5, 1972, now U.S. Pat. No. 3,849,402.

17β,19-Dihydroxyandrosta-4,6,8(14)-trien-3-one could also be obtained when a solution of 19-hydroxy-17β-pivaloxyandrosta-4,6,8(14)-trien-3-one and 2 N methanolic potassium hydroxide was heated for 16 hours at 70° C. under nitrogen. Isolation by conventional methods afforded 17β,19-dihydroxyandrosta-4,6,8(14)-trien-3-one as evidenced by tlc comparison with the product obtained above.

EXAMPLE 18

A mixture of 20 mg. of 3β,20β,19-trihydroxypregna-4,6,8(14)-triene, 18 mg. of dichlorodicyanoquinone and 2 ml. of ether was shaken under nitrogen for 40 minutes whereupon 2.0 ml. of half-saturated aqueous sodium bisulphite and 2.0 ml. of ethyl acetate was added. The organic phase was then extracted several times with 2% of aqueous potassium hydroxide until the extracts were alkaline and then with water. Evaporation at reduced pressure afforded a residue which on recrystallization with benzene-hexane yielded 19,20β-dihydroxypregna-4,6,8(14)-trien-3-one, mp. 206°–207° C., λ max 349 mμ.

EXAMPLE 19

3β,20β-Dihydroxy-19-nonpregna-4,6,8(14)-triene, when subjected to the reaction conditions of Example 18 afforded 20β-hydroxy-19-norpregna-4,6,8(14)-trien-3-one, mp. 162°–163° C., λ max 347 mμ.

EXAMPLE 20

Ergosta-4,7,22-trien-3-one, when subjected to the conditions of Example 1 afforded ergosta-4,6,8(14),22-tetraen-3-one, mp. 112°–113° C., λ max 250 mμ.

EXAMPLE 21

To a boiling solution of 50 mg. of ergosta-4,7,22-trien-3-one in 5 ml. of toluene was added 250 mg. of activated manganese dioxide. The mixture was refluxed for 5 hours under nitrogen, whereupon it was filtered through diatomaceous earth. Evaporation at reduced pressure gave a material containing ergosta-4,6,8(14),22-tetraen-3-one as the major product as indicated by tlc. and uv-spectroscopy, which may then be purified by chromatography.

EXAMPLE 22

A solution of 50 mg. of ergosta-4,7,22-trien-3-one in 5 ml. of ether was shaken with 50 mg. of dichlorodicyanoquinone under nitrogen for 2 days, whereupon it was extracted successively with half-saturated sodium bisulphite, several lots of aqueous 2% potassium hydroxide till the extracts were basic and then with water. Evaporation gave a material containing ergosta-4,6,8(14),22-tetraen-3-one as the major product as indicated by tlc and uv-spectroscopy, which may then be purified by chromatography.

EXAMPLE 23

A solution of 100 mg. of ergosta-4,7,22-trien-3-one in 10 ml. of xylene was brought to reflux under nitrogen, whereupon 100 mg. of chloranil was added. The mixture was then further refluxed under nitrogen for 22 hours whereupon it was diluted with 3 volumes of hexane and cooled at −5° C. for 3 hours. A viscous precipitate formed. The supernatant liquid was decanted, diluted further with hexane, treated with diatomaceous earth and filtered through diatomaceous earth. Successive extractions with half-saturated aqueous sodium bisulphite, several lots of 2% aqueous potassium hydroxide, till the extracts were alkaline, and water gave a material containing ergosta-4,6,8(14),22-tetraen-3-one as the major product as indicated by tlc and uv-spectroscopy, which may then by purified by chromatography.

EXAMPLE 24

A mixture of 100 mg of 19-hydroxy-20β-pivaloxypregna-4,6,8(14)-trien-3-one, 0.4 ml of pyridine and 0.2 ml of acetic anhydride was left to stand under nitrogen at room temperature for 16 hours, whereupon 12 ml of water and 24 ml of ether was added. The organic phase was extracted 3 times with water, dried with sodium sulfate and evaporated. The residue was recrystallized with petroleum ether-hexane to yield 91.3 mg of 18-acetoxy-20β-pivaloxypregna-4,6,8(14)-trien-3-one, ir (KBr) 3055, 3030, 1735, 1720, 1665, 1590, 1280, 1245, 1230, 1165, 1135, 1065, 1045, 920 and 880 cm$^{-1}$.

EXAMPLE 25

To a mixture of 5 mg of 19,21-dihydroxypregna-4,6-dien-3,20-dione in 0.05 ml of dimethylsulfoxide was added against a stream of nitrogen, 10 mg of sodium methoxide. The mixture was stirred well for 25 seconds and then cooled by a dry ice-hexane bath. A solution of 4.0 mg of 4,5-dichloro-3,6-dioxo-1,4-cyclohexadien-1,2-dicarbonitrile in 0.05 ml of acetic acid and 0.5 ml of ether was added. After 30 minutes of stirring in the dry ice bath the mixture was left to cool to 0° C. and 0.2 ml of aqueous half-saturated sodium bisulfite was added, followed by approximately 0.25 ml of water. The ethereal phase was extracted 4 times with 2% aqueous potassium hydroxide and then with concentrated ammonia-water 1:10. Evaporation of the ethereal phase gave a resin having UV max 347 mμ and consisting essentially of 19,21-dihydroxypregna-4,6,8(14)-trien-3,20-dione.

EXAMPLE 26

A mixture of 5 g of 19-hydroxy-17β-pivaloxyandrosta-4,6,8(14)-trien-3-one and 50 ml of methanol was cooled below 5° C. by an ice-bath, whereupon 500 mg. of sodium borohydride was added slowly and with stirring. After 85 minutes another 50 mg of sodium borohydride was added. The mixture was stirred with cooling for another 35 minutes, whereupon 10 ml of acetic acid-water 1:10 was added dropwise. After 10 minutes of further stirring without external cooling 2 g of sodium bicarbonate was added. The mixture was then concentrated at reduced pressure to a thick paste and 50 ml of water was added. The precipitate obtained was filtered and digested with benzene to yield 3β,19-dihydroxy-17β-pivaloxyandrosta-4,6,8(14)-triene, uv max 275 (sh), 285 and 300 (sh) mμ.

EXAMPLE 27

To a mixture of 4.5 g of 19-hydroxyandrost-4,6,8(14)-trien-3,17-dione in 40 ml of methanol, which was cooled externally by an ice-bath, was added 1.8 g of sodium borohydride with stirring. Stirring was continued for 1 hour, 450 ml of benzene was added and the mixture was concentrated at reduced pressure to a small volume. Benzene and a small volume of water was added and the mixture was concentrated again. Subsequent filtration and recrystallization of the precipitate from methanol gave 3β,17β,19-trihydroxyandrosta-4,6,8(14)-triene as a white solid, uv max 275 (sh), 285 and 298 (sh) mμ.

EXAMPLE 28

A mixture of 500 mg of 3β,17β,19-trihydroxyandrosta-4,6,8(14)-triene, 1.0 ml of pyridine and 0.5 ml of acetic anhydride was left to stand at room temperature for 16 hours in an atmosphere of nitrogen. Dilution with water, followed by extraction with ether and concentration at reduced pressure gave 3β,17β,19-triacetoxyandrosta-4,6,8(14)-triene as a white crystalline product.

EXAMPLE 29

A mixture of 100 mg of 19-hydroxy-20β-pivaloxypregna-4,6,8(14)-trien-3-one, 300 mg of lithium tri-t-butoxyaluminium hydride and 2 ml of tetrahydrofuran was agitated for 3 hours at room temperature. The mixture was then concentrated in the presence of benzene and the gelatinous precipitate obtained was treated with 10% aqueous acetic acid. Extraction with ethyl acetate, followed by washing of the organic phase with water and evaporation at reduced pressure in the presence of hexane gave, after filtration, 3β,19-dihydroxy-20β-pivaloxypregna-4,6,8(14)-triene, uv max 275 (sh), 286 and 299 (sh) mμ; mp 162°–163° C.

EXAMPLE 30

A mixture of 200 mg 19-hydroxy-20β-pivaloxypregna-4,6,8(14)-trien-3-one, 4 ml of tetrahydrofuran and 400 mg lithium tri-t-butoxyaluminium hydride was agitated under nitrogen at room temperature for 90 minutes, whereupon 200 mg of additional lithium tri-t-butoxyaluminium hydride was added. The mixture was then agitated for another 30 minutes and 0.8 ml of a 70% solution of sodium bis(methoxyethoxy) aluminium hydride in benzene ("Red-al") was added, followed after 10 minutes by an additional 0.4 ml of the latter reagent. The mixture was then left to stand for 80 minutes and methanol was added gradually until an additional amount of methanol ceased to produce gas-evolution. The mixture was concentrated to a gel at reduced pressure in the presence of hexane, treated with 10% aqueous acetic acid and hexane, and filtered. The precipitate obtained was treated with ethyl acetate-methanol 20:1 and filtered. The filtrate was concentrated at reduced pressure and the residue obtained was digested with pentane. Filtration gave 3β,19,20-trihydroxypregna-4,6,8(14)-triene; uv max 275 (sh), 281 and 300 (sh) mμ; ir (KBr) 3435, 3350, 3280 (sh), 1575 and 1410 cm⁻¹.

EXAMPLE 31

A mixture of 300 mg of 3β,19-dihydroxy-20β-pivaloxypregna-4,6,8(14)-triene and 3.0 ml of dimethylformamide-concentrated hydrochloric acid 200:1 was stirred magnetically at room temperature in the dark in an atmosphere of nitrogen for 175 minutes, whereupon 60 mg of 5% palladium on charcoal was added and the nitrogen atmosphere was exchanged for a hydrogen atmosphere. Stirring was continued for another 95 minutes, whereupon part of the mixture was withdrawn diluted with ethyl acetate and filtered through filter pulp in an atmosphere of nitrogen. The filtrate was extracted with water until the aqueous extracts were neutral and then evaporated yielding 19-hydroxy-20β-pivaloxypregna-4,6,8(14)-triene, uv max 295 (shoulder), 282 (major peak) and 272 (shoulder) mμ, as the major product. The remainder of the mixture was worked up as above after it had been stirred in the hydrogen atmosphere for 24 hours yielding a product which 19-hydroxy-20β-pivaloxypregna-8(14)-ene, uv max 211 mμ, was isolated by several recrystallizations from methanol, aqueous methanol, and hexane.

EXAMPLE 32

A mixture of 200 mg of 3β,19-dihydroxy-20β-pivaloxypregna-4,6,8(14)-triene and 2.0 ml of freshly prepared dimethylformamide-concentrated hydrochloric acid 200:1 was shaken under nitrogen at room temperature for 110 minutes, whereupon 6 ml of water was added. The mixture was left to stand under nitrogen at +5° for 90 minutes and was then filtered. The precipitate obtained was dissolved in methylene chloride, hexane was added until the solution was slightly turbid. Filtration through diatomaceous earth, concentration of the filtrate with intermittant addition of hexane, standing at −5° for 30 minutes and filtration gave 123 mg of 19-hydroxy-20β-pivaloxypregna-2,4,6,8(14)-tetraene, uv max 537 (shoulder), 341 (major peak), 325 (shoulder), 255 (shoulder), 247 and 240 mμ. Treatment of 2 mg of the latter compound with formic acid by the method described in the subsequent example gave the corresponding 19-formate, as evidenced by tlc analysis and hydrolysis to the starting material.

EXAMPLE 33

A mixture of 100 mg of 19-hydroxy-20β-pivaloxypregna-4,6,8(14)-triene-3-one 7.5 ml of toluene and 2.5 ml of 90% formic acid was shaken at room temperature under nitrogen for 2½ days, whereupon it was evaporated. Treatment with ether hexane 1:1, addition of charcoal, filtration through diatomaceous earth, concentration of the filtrate at reduced pressure, standing at −5° for 16 hours and filtration of the precipitate obtained gave 78.9 mg of 19-hydroxy-20β-pivaloxypregna-4,6,8(14)-trien-3-one, 19-formate, uv max 346 mμ, as evidenced by thin layer chromatography and hydrolysis of a sample to the starting material in methanol-aqueous ammonia.

The embodiments of the invention in which an exclusive property or privilege is claimed are defined as follows:

1. A process for preparing a compound of the formula

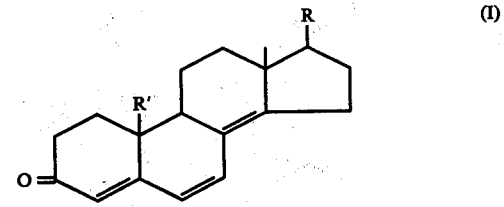

wherein R is selected from the group consisting of: O-acyl;

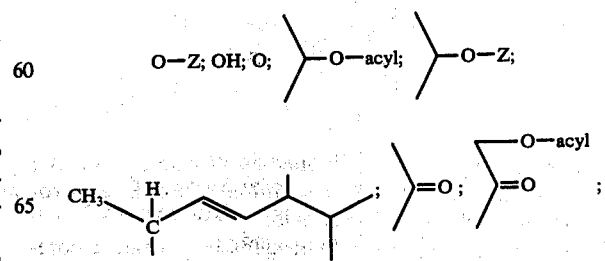

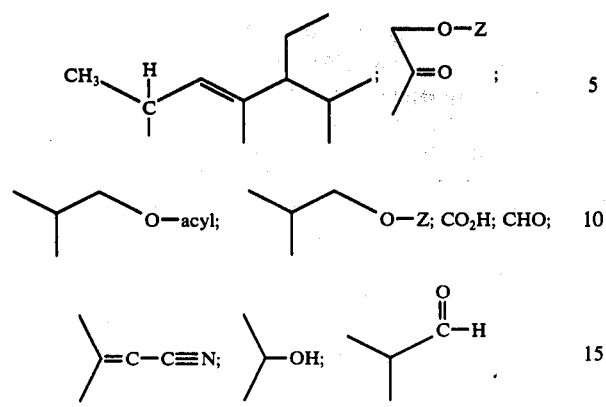

and CN, wherein Z is selected from the group consisting of tetrahydropyranyl, lower alkyl and substituted methyl, wherein the substituent on said methyl is selected from the group consisting of phenyl, $CH_2=CH$ and $HC\equiv C$; and acyl is selected from the group consisting of acetate, tri-lower-alkyl acetate, monohalo acetate and trihalo acetate; and R' is selected from the group consisting of: $CH_3$; $CH_2OH$; $CH_2$—O—CO—NH—$C(CH_3)_3$; $CH_2OCOCH_3$; CHO and H, which process is selected from the group consisting of a. treating, with a base, a compound chosen from

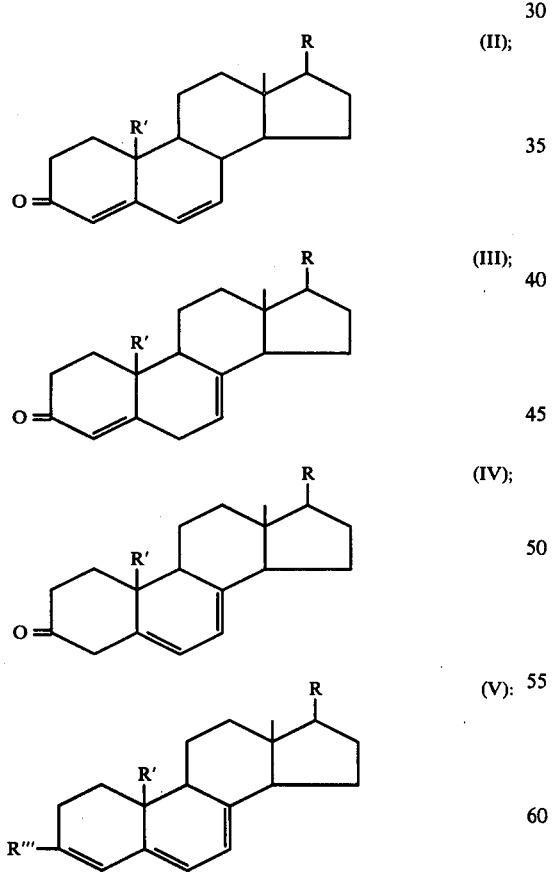

wherein R and R' are as defined above and R''' is AcO; and treating the resulting basic mixture with a dehydrogenating agent and a weak acid;

b. reacting, with a dehydrogenating agent, a compound chosen from

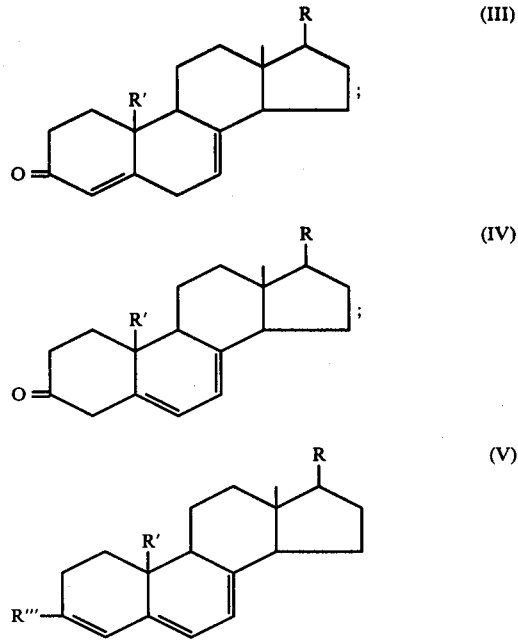

wherein R and R' are as defined above, and R''' is AcO or OH;

c. treating, with ferric chloride and methanol, a compound of the formula (VI), and treating the intermediate obtained, of the formula (VII), with a strong mineral acid wherein R is as defined above and said compounds (VI) and (VII) have the formula

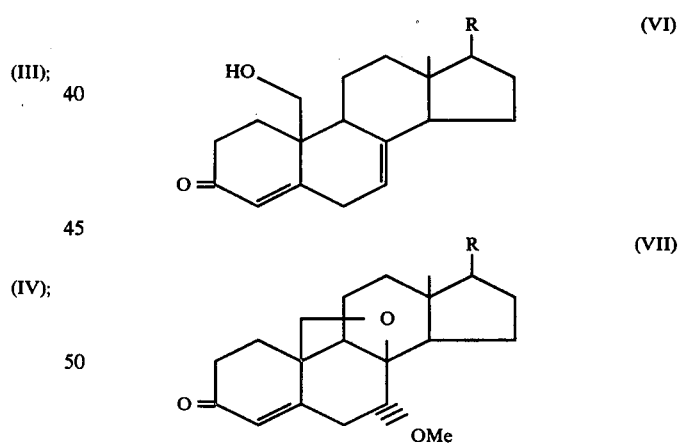

d. treating, with a peracid, a compound of the formula

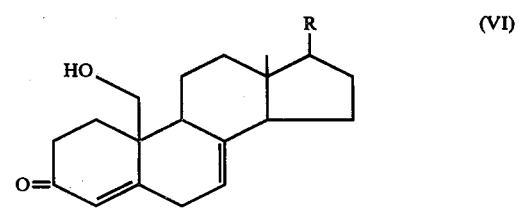

wherein R is as defined above, to form a mixture of compounds having the formula

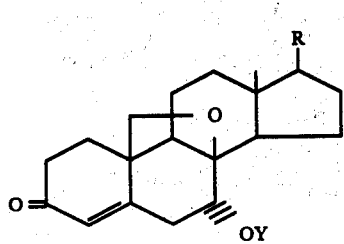 (VII)

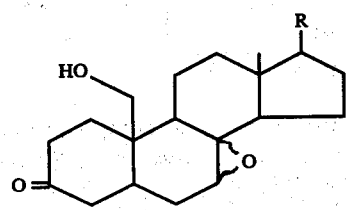 (VIII)

wherein R is as defined above and Y is hydrogen, and if desired separating from said mixture the 7-hydroxy compound and acetylating, if desired, said 7-hydroxy compound to form a corresponding 7-acetoxy compound, reacting said mixture, said 7-hydroxy compound or said 7-acetoxy compound with a strong mineral acid;

e. treating, with a base, a compound of the formula

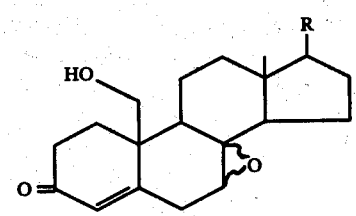 (VIII)

wherein R is as defined above, to form a mixture of compounds of the formula

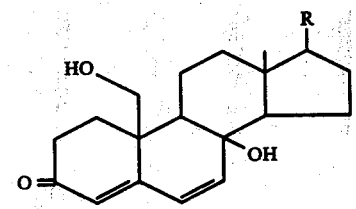 (IX)

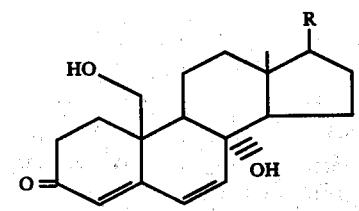 (X)

wherein R is as defined above, and treating said mixture with a dehydrating agent;

f. reacting, with a peracid, a compound of the formula

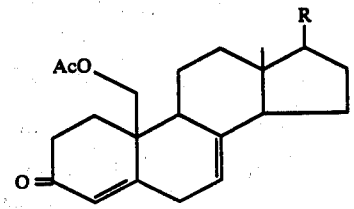 (XI)

wherein R is as defined above, and treating the intermediate obtained with a base, and subsequently dehydrating the resulting compound of formula (X); and g. reacting, with a peracid, a compound of the formula

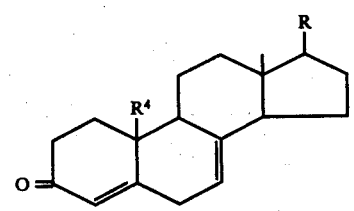 (XIII)

wherein R is as defined above and $R^4$ is chosen from H; $CH_3$; and $CH_2-O-CO-NH-C(CH_3)_3$, reacting the intermediate obtained with a base to form a compound of the formula

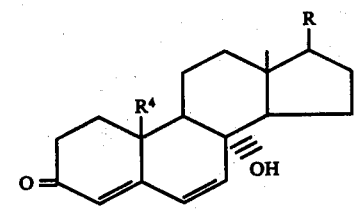 (XV)

wherein R and $R^4$ are as defined above, and treating the latter compound with a dehydrating agent.

2. A process as defined in claim 1, said process being for the preparation of a compound of the formula

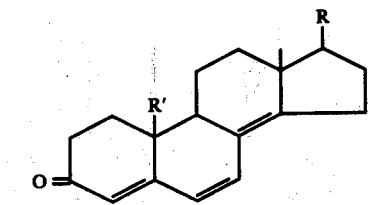 (I)

wherein R is selected from the group consisting of O-acyl,

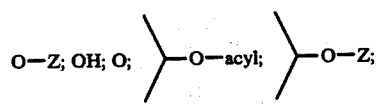

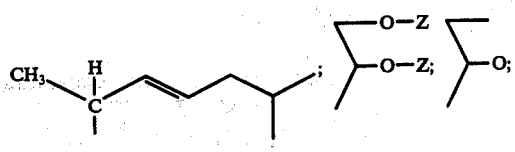

-continued

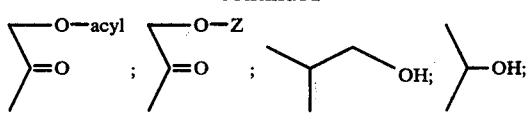

and CN; wherein Z is selected from the group consisting of tetrahydropyranyl, lower alkyl and substituted lower alkyl, and acyl is selected from the group consisting of acetate, formate, tri-lower-alkyl acetate, monohalo acetate, and trihalo acetate, and wherein R' is selected from the group consisting of CH₂OH and CHO, which process comprises:

a. treating, with a base, a compound chosen from

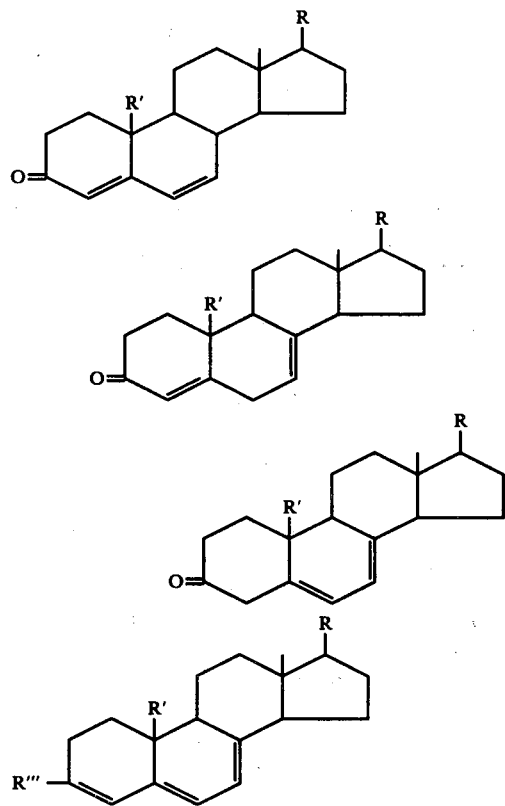

wherein R and R' are as defined above and R''' is AcO; and b. treating the resulting basic mixture with a dehydrogenating agent and a weak acid.

3. A compound of the formula

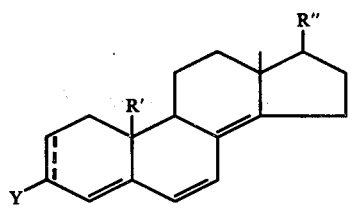

wherein R'' is selected from the group consisting of O-Z;

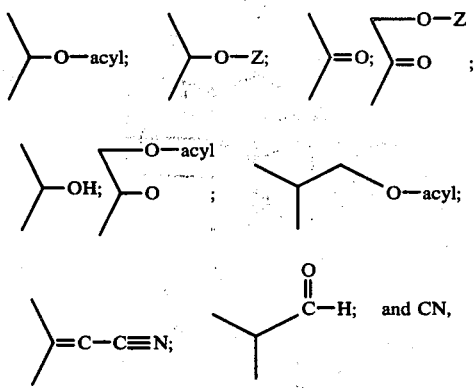

wherein Z is selected from the group consisting of: tetrahydropyranyl, lower alkyl, and substituted methyl, wherein the substituent is selected from the group consisting of phenyl, CH₂=CH and HC≡C; acyl represents a member selected from the group consisting of acetate, tri-lower-alkyl acetates, monohalo acetates and trihalo acetates; R' is selected from the group consisting of: CH₃; CH₂OH; CH₂—O—CO—NH—C(CH₃)₃; CH₂OCOCH₃; CHO and H; the broken line represents an optional double bond; and Y is selected from the group consisting of keto, OH, H, OZ and acyl with the proviso that when Y is keto there is no optional double bond present in the compound.

4. A compound as defined in claim 3, wherein the Z is selected from the group consisting of tetrahydropyranyl and methyl, and the acyl group is chosen from acetate, trimethyl acetate, triethyl acetate, chloroacetate, bromoacetate, trichloroacetate and tribromoacetate.

5. A compound as defined in claim 3, said compound having the formula:

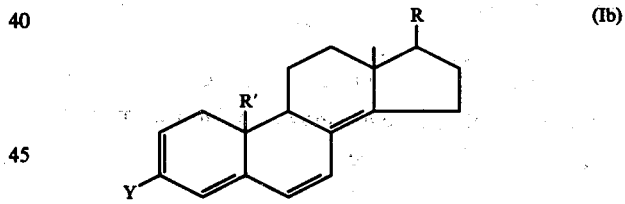

wherein R is selected from the group consisting of : O-Z;

and Y represents a member selected from the group consisting of H or O-acyl; wherein Z is selected from the group consisting of: tetrahydropyranyl, lower alkyl, and substituted methyl wherein the substituent is selected from the group consisting of phenyl, halogen, methoxy, CH₂=CH and HC≡C; acyl represents a member selected from the group consisting of: acetate; trilower-alkyl acetates, monohalo acetates, trihalo acetates, and R' is selected from the group consisting of CH₂OH and CHO.

6. A compound as defined in claim 3, said compound having the formula:

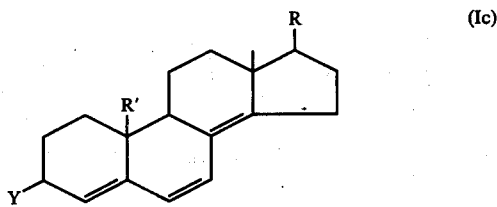

wherein R is selected from the group consisting of: O—Z;

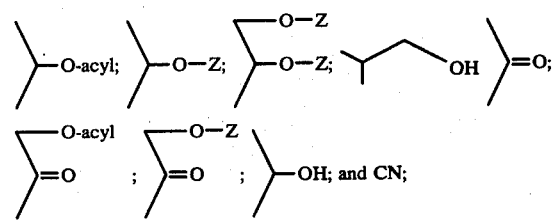

and Y represents a member selected from the group consisting of: keto, OH, H, O-Z and O-acyl; wherein Z is selected from the group consisting of tetrahydropyranyl, lower alkyl, and substituted methyl wherein the substituent is selected from the group consisting of: phenyl, halogen, methoxy, CH₂=CH and HC≡C; acyl represents a member selected from the group consisting of: acetate, trilower-alkyl acetates, monohalo acetates and trihalo acetates, and R' is selected from the group consisting of CH₂OH and CHO.

7. Compounds as defined in claim 5, wherein Z is tetrahydropyranyl.

8. Compounds as defined in claim 6, wherein Z is methyl.

9. Compounds as defined in claim 6, wherein Z is substituted methyl wherein the substituent is selected from the group consisting of phenyl, chlorine, bromine, methoxy, CH₂=CH and HC≡C.

10. Compounds as defined in claim 6, wherein the acyl group is an acetyl group.

11. Compounds as defined in claim 6, wherein the acyl group is a trimethylacetyl group.

12. A compound as defined in claim 6, wherein the compound is 19-hydroxy-20β-pivaloxypregna-4,6,8(14)-triene.

13. A compound as defined in claim 6, wherein the compound is 3β, 19-dihydroxy-20β-pivaloxypregna-4,6,8(14)-triene.

14. A compound as defined in claim 5, wherein the compound is 19-hydroxy-20β-pivaloxypregna-2,4,6,8(14)-tetraene.

15. A compound as defined in claim 5, wherein the compound is 19-formyloxy-20β-pivaloxypregna-2,4,6,8(14)-tetraene.

16. A compound as defined in claim 6, wherein the compound is 3β,19-dihydroxy-17β-pivaloxyandrosta-4,6,8(14)-triene.

17. A compound as defined in claim 6, wherein the compound is 3β, 17β, 19-trihydroxyandrosta 4,6,8(14)-triene.

18. A compound as defined in claim 6, wherein the compound is 3β, 17β-19-triacetoxyandrosta 4,6,8(14)-triene.

19. A compound as defined in claim 6, wherein the compound is 19-hydroxy-17β-pivaloxyandrosta-4,6,8(14)-trien-3-one.

20. A compound as defined in claim 6, wherein the compound is 19-hydroxy-17β-oxo-androsta-4,6,8(14)-trien-3-one.

21. A compound as defined in claim 6, wherein the compound is 17β,19-dihydroxyandrosta-4,6,8(14)-trien-3-one.

22. A compound as defined in claim 6, wherein the compound is 19,20β-dihydroxypregna-4,6,8(14)-trien-3-one.

23. A compound as defined in claim 6, wherein the compound is 19-hydroxy-20β-pivaloxypregna-4,6,8(14)-trien-3-one.

24. A compound as defined in claim 6, wherein the compound is 19-acetoxy-20β-pivaloxypregna-4,6,8(14)-trien-3-one.

25. A compound as defined in claim 6, wherein the compound is 19-formyloxy-20β-pivaloxypregna-4,6,8(14)-trien-3-one.

26. A compound as defined in claim 6, wherein the compound is 19,21-dihydroxypregna-4,6,8(14)-trien-3,20-dione.

27. A compound as defined in claim 6, wherein the compound is 3-oxo-20β-pivaloxypregna-4,6,8(14)-trien-19-al.

28. A compound as defined in claim 6, wherein the compound is 3β,19,20β-trihydroxypregna-4,6,8(14)-triene.

29. A process as defined in claim 2, wherein the 3-keto group is reduced to a 3-hydroxy analog.

30. A process as defined in claim 29, wherein the 3-hydroxy compound is subjected to acylation or alkylation to yield the corresponding 3-acyloxy or 3-alkyloxy analog.

31. A process as defined in claim 30, wherein the 3-substituted compound is dehydrated to yield the corresponding 2-dehydro analog.

32. A process as defined in claim 31, which comprises the further step of selectively hydrogenating the double bond in the position 2 to yield the corresponding triene analog.

33. A process as defined in claim 2, wherein the 3-keto compound is treated with an enol acylate to yield a member selected from the group consisting of (a) the corresponding 2-dehydro analog, and (b) a 3-O-acyl analog.

* * * * *